United States Patent
Shuster et al.

(10) Patent No.: US 6,794,180 B2
(45) Date of Patent: Sep. 21, 2004

(54) MORPHOLOGICAL MUTANTS OF FILAMENTOUS FUNGI

(75) Inventors: Jeffrey R. Shuster, Chapel Hill, NC (US); John C. Royer, Lexington, MA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 10/374,247

(22) Filed: Feb. 25, 2003

(65) Prior Publication Data

US 2004/0009579 A1 Jan. 15, 2004

Related U.S. Application Data

(63) Continuation of application No. 08/816,239, filed on Mar. 13, 1997, now Pat. No. 6,066,493, which is a continuation-in-part of application No. 08/726,114, filed on Oct. 4, 1996, now abandoned.
(60) Provisional application No. 60/010,238, filed on Jan. 19, 1996.

(51) Int. Cl.$^7$ .............................. C12N 1/14; C12N 1/16; C12N 1/18
(52) U.S. Cl. ................................ 435/254.4; 435/254.3; 435/254.8; 435/254.11; 435/173.1; 435/69.1
(58) Field of Search .......................... 435/254.4, 254.3, 435/173.1, 254.11, 254.8, 69.1

(56) References Cited

U.S. PATENT DOCUMENTS

| | | | | |
|---|---|---|---|---|
| 5,536,661 A | * | 7/1996 | Boel et al. | 435/254.3 |
| 5,578,463 A | * | 11/1996 | Berka et al. | 435/69.1 |
| 5,602,004 A | * | 2/1997 | Jensen et al. | 435/69.1 |
| 6,066,493 A | * | 5/2000 | Shuster et al. | 435/254.3 |
| 6,184,026 B1 | * | 2/2001 | Shuster et al. | 435/254.6 |

OTHER PUBLICATIONS

Wösten et al., J. of General Microbiology, vol. 137,p. 2017–2023,1991.
Wiebe et al., J. of General Microbiology, vol. 139, p. 2811–2817,1993.
Springer et al., Genes & Development, vol. 3, p. 559–571, 1989.
Rodrigues et al., Mycol. Res., vol. 95, No. 2, p. 169–177, 1991.
Pomés et al., FEMS Microbiology Letters, vol. 48, p. 255–259, 1987.
Withers et al., Mycol. Res., vol. 98, No. 1, p. 95–100, 1994.
Rosato et al., Rev. Braisil. Genet. X, vol. 3, p. 425–433, 1987.
Moscoso et al., Appl. Microbiology Biotechnology, vol. 26, p. 365–368, 1987.
Almeida et al., Trans. Br. Mycol. Soc., vol. 1, p. 139–143, 1984.
Banerjee et al., Can. J. Microbiol. vol. 27, p. 367–369, 1981.
Koide et al., J. Gen. Appl. Microbiol. vol. 25, p. 161–168, 1979.
Simpson et al., J. of General Microbiology, vol. 110, p. 1–12, 1979.

* cited by examiner

Primary Examiner—Christopher R. Tate
(74) Attorney, Agent, or Firm—Robert L. Starnes

(57) ABSTRACT

The present invention relates to methods of obtaining a mutant cell from a filamentous fungal parent cell, comprising: (a) obtaining mutant cells of the parent cell; (b) identifying the mutant cell which exhibits a more restricted colonial phenotype and/or a more extensive hyphal branching than the parent cell; and (c) identifying the mutant cell which has an improved property for production of a heterologous polypeptide than the parent cell, when the mutant and parent cells are cultured under the same conditions.

19 Claims, 11 Drawing Sheets

MORPHOLOGICAL MUTANTS OF FILAMENTOUS FUNGI

CROSS-REFERENCE TO RELATED APPLICATIONS

This application is a continuation of U.S. application Ser. No. 08/816,239 filed Mar. 13, 1997, now U.S. Pat. No. 6,066,493, which is a continuation-in-part of U.S. application Ser. No. 08/726,114 filed Oct. 4, 1996, now abandoned, which claims priority from U.S. provisional application Ser. No. 60/010,238 filed Jan. 19, 1996, which applications are fully incorporated herein by reference.

BACKGROUND OF THE INVENTION

1. Field of the Invention

The present invention relates to novel fungi having improved capacity for secretion of recombinant polypeptides, and a method for improving such secretion.

2. Description of the Related Art

Filamentous fungi have become established as widely used host cell systems for the production of recombinant polypeptides. In many cases, however, fungi which have the desirable traits of ease of transformability and heterologous polypeptide expression do not necessarily have the most desirable characteristics for successful fermentation. For example, growth morphology during fermentation may not be optimal, since many cultures become quite viscous as biomass increases. Increased viscosity limits the ability to mix and aerate the fermentation culture, leading to oxygen and nutrient starvation of the mycelia, which in turn become inviable and unproductive limiting the yield of the polypeptide of interest. On the other hand, filamentous fungal strains showing good fermentation morphology are not necessarily the best production strains in terms of quantity of enzyme produced. Therefore, for commercial purposes, there is a need for filamentous fungal hosts which combine the capacity for expression of commercial quantities of recombinant polypeptide with satisfactory growth characteristics, such as rapid growth and low viscosity, thereby enhancing productivity during fermentation.

Screening of large numbers of mutants for improved fermentation morphology is quite difficult, and morphological mutant strains have often been isolated based on unusual colony morphology on solid medium. Traditionally, morphological mutants have been isolated in transformed strains that contain multiple copies of a heterologous gene. The mutants are then analyzed for fermentation growth characteristics and heterologous gene expression. Although this method may be useful in identifying improved expression strains, the relationship between any particular fungal growth morphology and a strain's ability to produce a large quantity of secreted polypeptide has yet to be established. Morphological mutants are also occasionally recovered in polypeptide expression improvement screens, following mutagenesis of a transformed strain, but again, the study of these strains has not led to any significant insight into the control of morphology. In addition, morphologically "improved" strains of parental strains containing heterologous gene expression cassettes are not suitable as general expression hosts since they cannot be used for the exclusive expression of other heterologous polypeptides.

It is an object of the present invention to provide methods for producing and identifying useful morphological mutants for heterologous polypeptide production.

SUMMARY OF THE INVENTION

The present invention relates to methods of obtaining a mutant cell from a filamentous fungal parent cell, comprising: (a) obtaining mutant cells of the parent cell; (b) identifying the mutant cell which exhibits a more restricted colonial phenotype and/or more extensive hyphal branching than the parent cell; and (c) identifying the mutant cell which has an improved property for production of a heterologous polypeptide than the parent cell, when the mutant and parent cells are cultured under the same conditions.

The invention also relates to mutant filamentous fungal cells produced by the methods of the present invention.

The present invention also relates to methods for producing a heterologous polypeptide, comprising: (a) culturing a mutant cell of the present invention which comprises a nucleic acid sequence encoding the heterologous polypeptide; and (b) recovering the heterologous polypeptide.

DETAILED DESCRIPTION OF THE INVENTION

Figure 1:
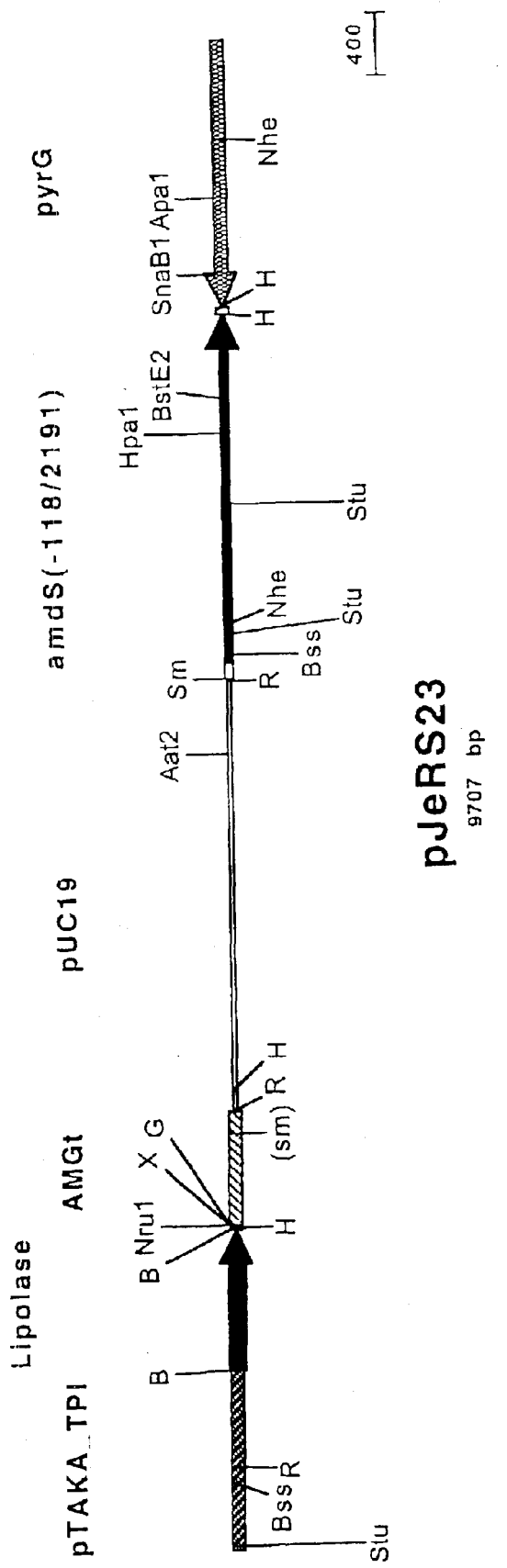
FIG. 1 shows a restriction map of pJeRS23.

The present invention relates to methods of obtaining a mutant cell from a filamentous fungal parent cell, comprising: (a) obtaining mutant cells of the parent cell; (b) identifying the mutant cell which exhibits a more restricted colonial phenotype and/or more extensive hyphal branching than the parent cell; and (c) identifying the mutant cell which has an improved property for production of a heterologous polypeptide than the parent cell, when the mutant and parent cells are cultured under the same conditions.

The parent cell may be mutagenized by methods known in the art. For example, mutagenesis of the parent cell can be achieved by irradiation, e.g., UV, X-ray, or gamma radiation of the parent cell. Furthermore, mutagenesis can be obtained by treatment with chemical mutagens, e.g., nitrous acid, nitrosamines, methyl nitrosoguanidine, and base analogues such as 5-bromouracil. Most conveniently, the mutagen is applied to spores of the parent strain, and the surviving spores are plated out for growth on a solid medium. It will also be understood that mutants can also be naturally occurring variants in a population in the absence of a specific mutagenesis procedure, either by selection, screening, or a combination of selection and screening. See, for example, Wiebe et al., 1992, *Mycological Research* 96: 555–562 and Wiebe et al., 1991, *Mycological Research* 95: 1284–1288 for isolating morphological mutants of Fusarium strain A3/5. Therefore, for purposes of the present invention, the term "mutants" also encompasses naturally occurring variants or mutants without deliberate application of mutagens, i.e., spontaneous mutants.

The filamentous fungal parent cell may be any filamentous fungal cell. Filamentous fungi include all filamentous forms of the subdivision Eumycota and Oomycota (as defined by Hawksworth et al., In, *Ainsworth and Bisby's Dictionary of The Fungi*, 8th edition, 1995, CAB International, University Press, Cambridge, UK). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic.

In the present invention, the filamentous fungal parent-cell may be a cell of a species of, but not limited to, Acremonium, Aspergillus, Fusarium, Humicola, Myceliophthora, Mucor, Neurospora, Penicillium, Thielavia, Tolypocladium, and Trichoderma or teleomorphs or synonyms thereof. Known teleomorphs of Aspergillus include Eurotium, Neosartorya, and Emericella. Strains of Aspergillus and teleomorphs thereof are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL). Known teleomorphs of Fusarium of the section Discolor include *Gibberella gordonii, Gibberella cyanea, Gubberella pulicaris,* and *Gibberella zeae.*

In a preferred embodiment, the filamentous fungal parent cell is an Aspergillus cell. In another preferred embodiment, the filamentous fungal parent cell is an Acremonium cell. In another preferred embodiment, the filamentous fungal parent cell is a Fusarium cell, e.g., a Fusarium cell of the section Elegans or of the section Discolor. In another preferred embodiment, the filamentous fungal parent cell is a Humicola cell. In another preferred embodiment, the filamentous fungal parent cell is a Myceliophthora cell. In another preferred embodiment, the filamentous fungal parent cell is a Mucor cell. In another preferred embodiment, the filamentous fungal parent cell is a Neurospora cell. In another preferred embodiment, the filamentous fungal parent cell is a Penicillium cell. In another preferred embodiment, the filamentous fungal parent cell is a Thielavia cell. In another preferred embodiment, the filamentous fungal parent cell is a Tolypocladium cell. In another preferred embodiment, the filamentous fungal parent cell is a Trichoderma cell. In a more preferred embodiment, the filamentous fungal parent cell is an *Aspergillus oryzae, Aspergillus niger, Aspergillus foetidus, Aspergillus nidulans,* or *Aspergillus japonicus* cell. In another more preferred embodiment, the filamentous fungal parent cell is a Fusarium strain of the section Discolor (also known as section Fusarium). For example, the filamentous fungal parent cell may be a *Fusarium bactridioides, Fusarium cerealis, Fusarium crookwellense, Fusarium culmorum, Fusarium graminearum, Fusarium graminum, Fusarium heterosporum, Fusarium negundi, Fusarium reticulatum, Fusarium roseum, Fusarium sambucinum, Fusarium sarcochroum, Fusarium sulphureum,* or *Fusarium trichothecioides* cell. In another prefered embodiment, the filamentous fungal parent cell is a Fusarium strain of the section Elegans, e.g., *Fusarium oxysporum*. In another more preferred embodiment, the filamentous fungal parent cell is a *Humicola insolens* or *Humicola lanuginosa* cell. In another more preferred embodiment, the filamentous fungal parent cell is a *Myceliophthora thermophilum* cell. In another more preferred embodiment, the filamentous fungal parent cell is a *Mucor miehei* cell. In another more preferred embodiment, the filamentous fungal parent cell is a *Neurospora crassa* cell. In another more preferred embodiment, the filamentous fungal parent cell is a *Penicillium purpurogenum* cell. In another more preferred embodiment, the filamentous fungal parent cell is a *Thielavia terrestris* cell. In another more preferred embodiment, the Trichoderma cell is a *Trichoderma reesei, Trichoderma viride, Trichoderma longibrachiatum, Trichoderma harzianum,* or *Trichoderma koningii* cell.

The mutant cells produced in the first step are then screened for those mutant cells which (a) exhibit a more restricted colonial phenotype and/or more extensive hyphal branching than the parent cell; and (b) have an improved property for production of a heterologous polypeptide than the parent cell, when the mutant and parent cells are cultured under the same conditions. In a preferred embodiment, the mutant cells are inspected first for the more restricted colonial phenotype and/or more extensive hyphal branching, more preferably, first for the more restricted colonial phenotype followed by the more extensive hyphal branching.

The mutant cells of the present invention may have a colonial phenotype which is more restricted than the parent cell when the mutant and parent cells are grown on the same solid medium. A mutant cell having "more restricted colonial phenotype" is defined herein as a mutant cell having a reduced radial extension rate than a parent cell when the mutant cell and parent cell are grown on the solid medium. Preferably, the colonial phenotype of the mutant cells is at least about 10%, more preferably at least about 20%, and most preferably at least about 30% more restricted than the parent cell.

The mutant cells of the present invention may also have a more extensive hyphal branching than the parent cell. A mutant cell having a "more extensive hyphal branching" is defined herein as a mutant cell having a hyphal growth unit length which is at least 10% less than the hyphal growth unit length of the parent cell. Preferably, the hyphal branching of the mutant cell is at least about 20% more branched, and more preferably at least about 30% more branched than the parent cell. Measurement of the hyphal growth unit length may be made according to the method of Trinci et al., 1973, *Archiv für Mikrobiologie* 91: 127–136. One way of making this determination is to measure the average distance between branches in fungal hyphae (see, for example, Withers et al., 1994, *Mycological Research* 98: 95–100).

The mutant cells of the present invention also have an improved property for production of a heterologous polypeptide than the parent cell, when the mutant and parent cells are cultured under the same conditions. The mutants obtained by the methods of the present invention may possess improved growth characteristics in fermentation where the morphology gives rise to lower viscosity in the fermenter, in turn leading to easier mixing, better aeration, better growth, and ultimately, enhanced yield of heterologous polypeptide produced by the mutant strain relative to the parent strain. In a preferred embodiment, the improved property is selected from the group consisting of (a) increased yield of the heterologous polypeptide, (b) improved growth, (c) lower viscosity, and (d) better secretion. In a most preferred embodiment, the improved property is increased yield of the heterologous polypeptide. In another most preferred embodiment, the improved property is improved growth. In another most preferred embodiment, the improved property is lower viscosity. In another most preferred embodiment, the improved property is better secretion.

In order to determine whether a mutant cell has an improved property for production of a heterologous polypeptide than the parent cell, a nucleic acid construct comprising a nucleic acid sequence encoding the heterologous polypeptide of interest is introduced into both the parent strain and the morphological mutant, e.g., by transformation. "Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The mutant cell is preferably transformed with a vector comprising the nucleic acid construct followed by integration of the vector into the host chromosome. "Transformation" means introducing a nucleic acid construct into a host cell so that the construct is maintained as a chromosomal integrant. Integration is generally considered to be an advantage as the nucleic acid sequence encoding the heterologous polypeptide is more likely to be stably maintained in the cell. Integration of the vector into the host chromosome occurs by homologous or non-homologous recombination. Transformation is achieved using those techniques adapted for the fungal host being used, many of which are well known in the art. Suitable procedures for transformation of Aspergillus cells are described in EP 238 023, Christensen et al., 1988, *Bio/Technology* 6:1419–1422, and Yelton et al., 1984, *Proceedings of the National Academy of Sciences USA* 81:1470–1474. A suitable method of transforming Fusarium species is described by Malardier et al., 1989, *Gene* 78:147–156 or in copending U.S. Serial No. 08/269,449.

After transformation of the mutant and the parent cell with a vector containing a gene encoding a heterologous polypeptide, spores gathered from the mutants and parent are used to inoculate liquid medium. After a suitable period of growth, supernatants are tested for activity of the polypeptide.

When the improved property is yield, the levels of expression of the heterologous polypeptide are compared between the mutant and parent strains. In such case, the productive phase of the mutant's fermentation should be extended. In a preferred embodiment, the morphological mutant produces at least about 10% more heterologous polypeptide than the parent strain when each strain is cultured under identical conditions. More preferably, the mutant produces at least 20%, and most preferably at least 30%, more heterologous polypeptide. In some cases, the mutant may produce as much as 50%–100% more polypeptide, or even higher. Since in all cultures it is expected that a range of expression levels may be observed, it is understood that this figure can represent the mean, median or maximum level of expression in a population of transformant strains.

When the improved property is reduced viscosity, viscosity can be determined by any means known in the art, e.g., Brookfield rotational viscometry (defined or unlimited shear distance and any type of spindle configuration), kinematic viscosity tubes (flow-through tubes), falling ball viscometer or cup-type viscometer. The preferred host cells of the present invention exhibit about 90% or less of the viscosity level produced by an the parent cell under identical fermentation conditions, preferably about 80% or less, and more preferably about 50% or less.

The present morphological mutants can be used to express any prokaryotic or eukaryotic heterologous peptide or polypeptide of interest, and are preferably used to express eukaryotic peptides or polypeptides. Of particular interest for these species is their use in expression of heterologous polypeptides, in particular fungal polypeptides, especially fungal enzymes. The morphological mutants can be used to express enzymes such as a hydrolase, an oxidoreductase, an isomerase, a ligase, a lyase, or a transferase. More preferably, the enzyme is an aminopeptidase, an amylase, a carboxypeptidase, a catalase, a cellulase, a chitinase, a cutinase, a cyclodextrin glycosyl transferase, a deoxyribonuclease, an esterase, a glucoamylase, an alpha-galactosidase, a beta-galactosidase, an alpha-glucosidase, beta-glucosidase, a haloperoxidase, an invertase, a laccase, a lipase, a mannosidase, a mutanase, an oxidase, a pectinolytic enzyme, a peroxidase, a phenoloxidase, phytase, a proteolytic enzyme, a ribonuclease, a xylanase, or a xylose isomerase. It will be understood by those skilled in the art that the term "fungal enzymes" includes not only native fungal enzymes, but also those fungal enzymes which have been modified by amino acid substitutions, deletions, additions, or other modifications which maybe made to enhance activity, thermostability, pH tolerance and the like. Other polypeptides that can be expressed include, but are not limited to, mammalian polypeptides such as insulin, insulin variants, receptor proteins and portions thereof, and antibodies and portions thereof.

The mutants may also be used in recombinant production of polypeptides which are native to the host cells. Examples of such use include, but are not limited to, placing a gene encoding the polypeptide under the control of a different promoter to enhance expression of the polypeptide, to expedite export of a native polypeptide of interest outside the cell by use of a signal sequence, or to increase the copy number of a gene encoding the protein normally produced by the subject host cells. Thus, the present invention also encompasses, within the scope of the term "heterologous polypeptide", such recombinant production of homologous polypeptides, to the extent that such expression involves the use of genetic elements not native to the host cell, or use of native elements which have been manipulated to function in a manner not normally seen in the host cell.

In the present invention, the nucleic acid construct is operably linked to one or more control sequences capable of directing the expression of the coding sequence in the mutant cell under conditions compatible with the control sequences. The term "coding sequence" as defined herein is a sequence which is transcribed into mRNA and translated into a polypeptide of the present invention when placed under the control of the control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcription and translation control sequences which mediate the expression of the polypeptide. The promoter may be any nucleic acid sequence which shows transcriptional activity in the host cell of choice and may be obtained from genes encoding extracellular or intracellular polypeptides either homologous or heterologous to the host cell. Examples of suitable promoters for directing the transcription of the nucleic acid constructs of the present invention in a filamentous fungal cell are promoters obtained from the genes encoding *Aspergillus oryzae* TAKA amylase (as described in U.S. patent application Ser. No. 08/208,092, the contents of which are incorporated herein by reference), *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal cells are the TAKA amylase, NA2-tpi (a hybrid of the promoters from the genes encoding *Aspergillus niger* neutral α-amylase and *Aspergillus oryzae* triose phosphate isomerase), and glaA promoters.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention. Preferred terminators for filamentous fungal cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of a mRNA which is important for translation by the host cell. The leader sequence is operably linked to the 5' terminus of the nucleic acid sequence encoding the polypeptide. Any leader sequence which is functional in the host cell of choice may be used in the present invention. Preferred leaders for filamentous fungal host cells are obtained from the genes encoding *Aspergillus oryzae* TAKA amylase and *Aspergillus oryzae* triose phosphate isomerase.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

The control sequence may also be a signal peptide coding region, which codes for an amino acid sequence linked to the amino terminus of the polypeptide which can direct the expressed polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from a glucoamylase or an amylase gene from an Aspergillus species, a lipase or proteinase gene from a Rhizomucor species, the gene for the alpha-factor from *Saccharomyces cerevisiae*, an amylase or a protease gene from a Bacillus species, or the calf preprochymosin gene. However, any signal peptide coding region capable of directing the expressed polypeptide into the secretory pathway of a host cell of choice may be used in the present invention. An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

The vector may be any vector which can be conveniently subjected to recombinant DNA procedures and can bring about the expression of the nucleic acid sequence encoding the polyppetide. The choice of the vector will typically depend on the compatibility of the vector with the host cell into which the vector is to be introduced. The vectors may be linear or closed circular plasmids. The vector system may be a single vector or plasmid or two or more vectors or plasmids which together contain the total DNA to be introduced into the genome of the host cell. The vectors of the present invention preferably contain an element(s) that permits stable integration of the vector into the host cell genome. For integration, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

The vectors preferably contain one or more selectable markers which permit easy selection of transformed cells. A selectable marker is a gene the product of which provides for biocide resistance, resistance to heavy metals, prototrophy to auxotrophs, and the like. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an Aspergillus cell are the amdS and pyrG markers of Aspergillus nidulans or Aspergillus oryzae and the bar marker of Streptomyces hygroscopicus. Furthermore, selection may be accomplished by co-transformation, e.g., as described in WO 91/17243, where the selectable marker is on a separate vector.

According to a preferred embodiment of the present invention, the host is transformed with a single DNA vector including both the selection marker and the remaining heterologous DNA to be introduced, including promoter, the gene for the desired polypeptide and transcription terminator and polyadenylation sequences.

The procedures used to ligate the elements described above to construct the nucleic acid constructs and vectors are well known to one skilled in the art (see, e.g., Sambrook et al., 1989, *Molecular Cloning: A Laboratory Manual*, Cold Spring Harbor Press, Cold Spring Harbor, N.Y.), 1989, supra).

The present invention also relates to methods of producing a heterologous polypeptide, comprising: (a) cultivating a mutant cell of the present invention which comprises a nucleic acid sequence encoding the heterologous polypeptide; and (b) recovering the heterologous polypeptide.

The cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi*, Academic Press, CA, 1991). Suitable media are available from commercial suppliers or maybe prepared according to published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining enzyme activity are well known in the art.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation. The recovered polypeptide may then be further purified by a variety of chromatographic procedures, e.g., ion exchange chromatography, gel filtration chromatography, affinity chromatography, or the like.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., *Protein Purification*, J.-C. Janson and Lars Ryden, editors, VCH Publishers, New York, 1989).

EXAMPLES

Strains and Media

The starting strains are alpha-amylase deficient, pyrG-negative *Aspergillus oryzae* HowB425 and *Fusarium* A3/5. Morphological mutants of *Fusarium* A3/5 designated CC1-3, CC2-3, and MC3-5 (Wiebe et al., 1992, *Mycological Research* 96: 555–562; Wiebe et al., 1991, *Mycological Research* 95: 1284–1288; Wiebe et al., 1991, *Mycological Research* 96: 555–562) are highly branched, colonial variants.

PDA plates contain 39 g/l Potato Dextrose Agar (Difco) and are supplemented with 10 mM uridine for pyrG auxotrophs unless otherwise indicated.

MY50N medium is comprised of 62.5 g of Nutriose, 2.0 g of $MgSO_4$-$7H_2O$, 2.0 g of $KH_2PO_4$, 4.0 g of citric acid, 8.0 g of yeast extract, 2.0 g of urea, 0.1 g of $CaCl_2$, and 0.5 ml of trace metals solution pH 6.0 per liter. MY50N shake-flask medium is diluted 1:100 with glass distilled water for use in microtiter growth experiments (MY50N/100). Cultures are grown at a temperature between 28–37° C.

Minimal medium plates are comprised of 6.0 g of $NaNO_3$, 0.52 g of KCl, 1.52 g of $KH_2PO_4$, 1.0 ml of trace metals solution, 20 g of Nobel Agar (Difco), 20 ml of 50% glucose, 20 ml of methionine (50 g/l), 20 ml of biotin (200 mg/l), 2.5 ml of 20% $MgSO_4$-$7H_2O$, and 1.0 ml of mg/ml streptomycin per liter. The agar medium is adjusted to pH 6.5 prior to autoclaving and then glucose, methionine, biotin, $MgSO_4$-$7H_2O$, and streptomycin are added as sterile solutions to the cooled autoclaved medium and poured into plates.

The trace metals solution (1000x) is comprised of 22 g of $ZnSO_4$-$7H_2O$, 11 g of $H_3BO_3$, 5 g of $MnCl_2$-$4H_2O$, 5 g of $FeSO_4$-$7H_2O$, 1.6 g of $CoCl_2$-$5H_2O$, 1.6 g of $(NH_4)_6Mo_7O_{24}$, and 50 g of $Na_4EDTA$ per liter.

COVE plates are comprised of 343.3 g of sucrose, 20 ml of COVE salts solution, 10 ml of 1 M acetamide, 10 ml of 3 M CsCl, and 25 g of Nobel agar per liter. The COVE salts (50x) solution is comprised of 26 g of KCl, 26 g of $MgSO_4$-$7H_2O$, 76 g of $KH_2PO_4$, and 50 ml of COVE trace metals solution. COVE trace metals solution is comprised of 0.04 g of $NaB_4O_7$-$10H_2O$, 0.040 g of $CuSO_4$-$5H_2O$, 0.70 g of $FeSO_4$—$H_2O$, 0.80 g of $Na_2MoO_2$-$2H_2O$, and 10 g of $ZnSO_4$ per liter.

M400Da medium is comprised of 50 g of maltodextrin, 2.0 g of $MgSO_4$-$7H_2O$, 2.0 g of $KH_2PO_4$, 4.0 g of citric acid, 8.0 g of yeast extract, 2.0 g of urea, and 0.5 ml of trace metals solution per liter. The medium is adjusted to pH 6.0 with 5 N NaOH. The trace metals solution is comprised of 14.3 g of $ZnSO_4\text{-}7H_2O$, 2.5 g of $CuSO_4\text{-}5H_2O$, 0.5 g of $NiCl_2\text{-}6H_2O$, 13.8 g of $FeSO_4\text{-}7H_2O$, 8.5 g of $MnSO_4\text{--}H_2O$, and 3.0 g of citric acid per liter.

Example 1

Mutagenesis of *Aspergillus oryzae* Strain HowB425

*Aspergillus oryzae* strain HowB425 spores are harvested from solid medium and suspended to a concentration of $2.2\times10^7$/ml in 0.01% Tween 80. Five ml of spore suspension are pipetted into a 90 mm plastic petri dish and the spores are irradiated for one minute with ultraviolet light to approximately 5% survival. The mutagenized spores are kept in the dark for one hour and then plated to PDA+50 mg/l uridine plates.

Figure 2:
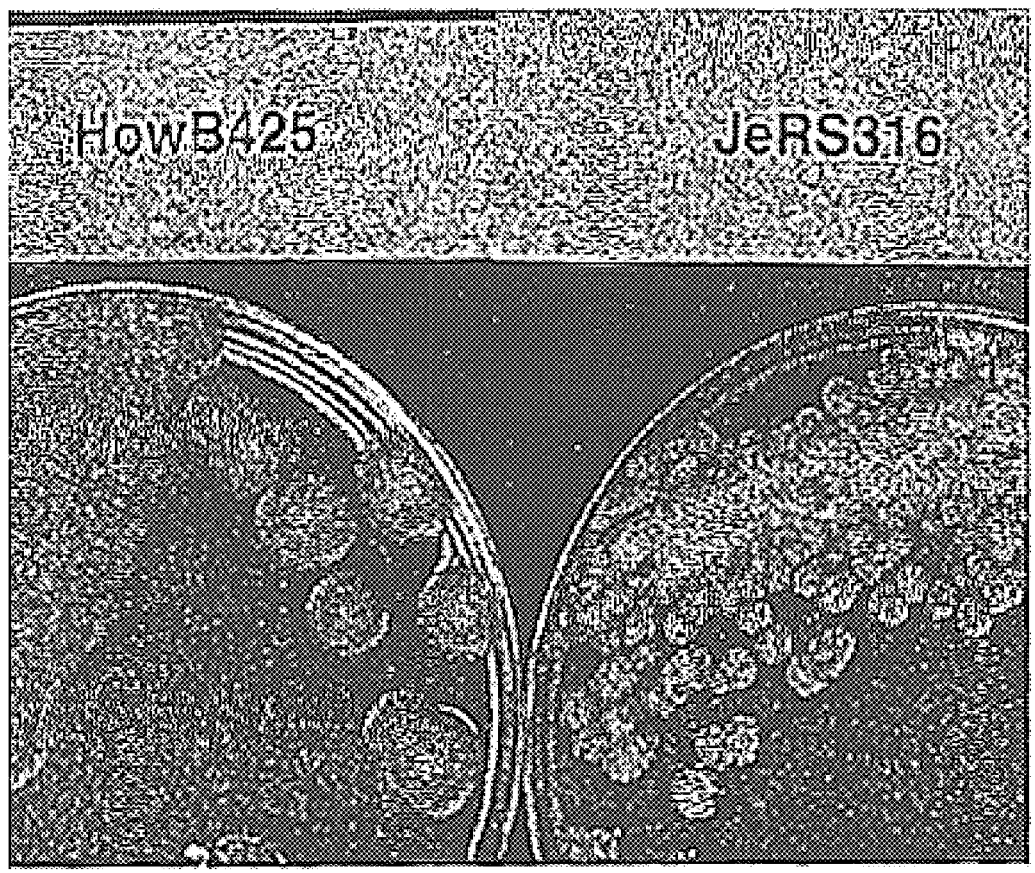
FIG. 2 shows the colony growth of control strain HowB425 and colonial mutant JeRS316 on PDA+uridine solid medium.

The frequencies of spore color mutants obtained from this mutagenesis treatment are $8.8\times10^{-5}$ for white and $5.9\times10^{-5}$ for yellow spored mutants. A total of about 34,000 viable colonies (250 to 800 per plate) are screened visually for a restricted colonial phenotype. Eighty-eight restricted colonials are selected. The edges of the restricted colonies growing on the plate are examined under a microscope (200x) for a high mycelial branching phenotype. Thirty-six of the selected colonials are selected as having a more extensive hyphal branching pattern than the *Aspergillus oryzae* HowB425 control strain and are purified by restreaking spores onto PDA+uridine plates. After growth and sporulation, the strains are repurified in a similar fashion. The 36 mutants are re-examined for the colonial and high-branching phenotypes. Twelve of the 36 retested positive in both assays and are selected for heterologous polypeptide expression analysis. The frequency of mutants recovered is $12/34,000$ or about $3.5\times10^{-4}$. The colonial mutants are classified by examination of their hyphal branching phenotypes (Table I). The colony morphology of the control strain and one of the mutants on PDA+uridine solid medium are shown in FIG. 2.

TABLE I

Phenotypes of Morphological Mutants

| Phenotypes | Strains |
| --- | --- |
| Wild Type growth and low branching | HowB425 (control) |
| Colonial growth and medium branching | JeRS306 |
| | JeRS307 |
| | JeRS314 |
| | JeRS316 |
| | JeRS318 |
| Colonial growth and high branching | JeRS303 |
| | JeRS304 |
| | JeRS315 |
| | JeRS320 |
| Colonial growth and very high branching | JeRS313 |
| Colonial growth and highly branched short hyphae | JeRS317 |
| Colonial growth and highly branched very short hyphae | JeRS305 |

Example 2

Lipase Expression Plasmid

A map of the lipase expression plasmid pJeRS23 is shown in FIG. 1. pJeRS23 contains the amdS gene from *Aspergillus nidulans* from bases-118 to 2191 (relative to the ATG start codon), the pTAKA-TPI/Lipolase/AMGt lipase expression cassette from pMHan37, the *Aspergillus oryzae* pyrG gene, and pUC19 sequences.

Example 3

*Aspergillus oryzae* Transformation

Cultures to be transformed are grown in 20 ml of 1% yeast extract-2% Peptone (Difco)-2.5% glucose at 37° C. for 16–20 hours with agitation. Each culture is mixed with 10 ml of 1.2 M $MgSO_4$, and the mycelia are recovered by filtration on Miracloth (CalBiochem, La Jolla, Calif.) or by centrifugation, washed with 1.2 M $MgSO_4$, and then resuspended in 10 ml of 5 mg/ml NOVOZYM 234 (Novo Nordisk A/S, Bagsvaerd, Denmark) in 1.2 M $MgSO_4$. The suspension is incubated with gentle agitation for approximately one hour at 37° C. to generate protoplasts. Undigested mycelia are removed by filtration through a layer of sterile Miracloth. Protoplasts are recovered by centrifugation at 3600×g. They are then washed with 10 ml of ST (1 M sorbitol-10 mM Tris pH 7.5), centrifuged, washed with 10 ml of STC (1 M sorbitol-10 mM Tris pH 7.5–10 mM $CaCl_2$), centrifuged, and then resuspended in 1.0 ml of STC. The concentration of protoplasts is determined and the final concentration is adjusted to between $2\times10^6$ and $1\times10^7$/ml with STC. An aliquot of 0.1 ml protoplasts is mixed with 5 $\mu$l of pJeRS23 DNA (about 5 $\mu$g) in a Falcon 2059 polypropylene tube and incubated at room temperature for 20 minutes. One ml of SPTC (0.8 M sorbitol-40% polyethylene glycol 4000–50 mM $CaCl_{2-50}$ mM Tris pH 8) is added and the suspension is mixed with gentle shaking. The suspension is incubated at room temperature for 20 minutes and then 7 ml of molten overlay agar (1×COVE salts, 0.8 M sucrose, 1% low melt agarose) is added and the suspension is poured onto a COVE plate. The plates are incubated at 37° C.

Example 4

Lipase Assay

Assay substrate is prepared by diluting 1:5 the stock substrate (10 $\mu$l of p-nitrophenylbutyrate/ml DMSO) into MC buffer (3 mM $CaCl_2$-0.1M MOPS pH 7.5) immediately before use. Standard Lipolase® contains 1000 LU/ml of 50% glycerol-0.66 mM $CaCl_2$-33 mM Tris pH 7.5 and is stored at −20° C. Standard Lipolase® is diluted 1/100 in MC buffer just before use. Broth samples are diluted in MC buffer and 100 $\mu$l aliquots of the diluted broth samples are pipetted into 96-well microtiter dishes followed by 100 $\mu$l of diluted substrate. The absorbance at nm is recorded as a function of time. Broth lipase units/ml (LU/ml) are calculated relative to a Lipolase® standard.

Example 5

Lipolase® Expression

Each of the twelve mutants is transformed with the Lipolase® expression plasmid pJeRS23 described in Example 2 and the transformants are selected by their prototrophy for uridine and ability to grow using acetamide as sole nitrogen source. A parallel transformation is performed with the parent strain *Aspergillus oryzae* HowB425. The conidiated transformants are restreaked once to COVE plates and spores from individual colonies are used to inoculate a 90 mm COVE plate. After sporulation, the spores are harvested in 0.01% Tween 80. A 10 $\mu$l aliquot of each spore suspension is used to inoculate a well in a 24-well microtiter plate that contains 1 ml of MY50N/100 liquid medium. Experiments are started on two different days (Experiments A and B) with the entire set of *Aspergillus oryzae* HowB425 control transformants included each day.

The microtiter plates are grown for 3–5 days at 37° C., 100 rpm agitation, and the culture supernatants are assayed for lipase activity as described in Example 4.

Figure 3:
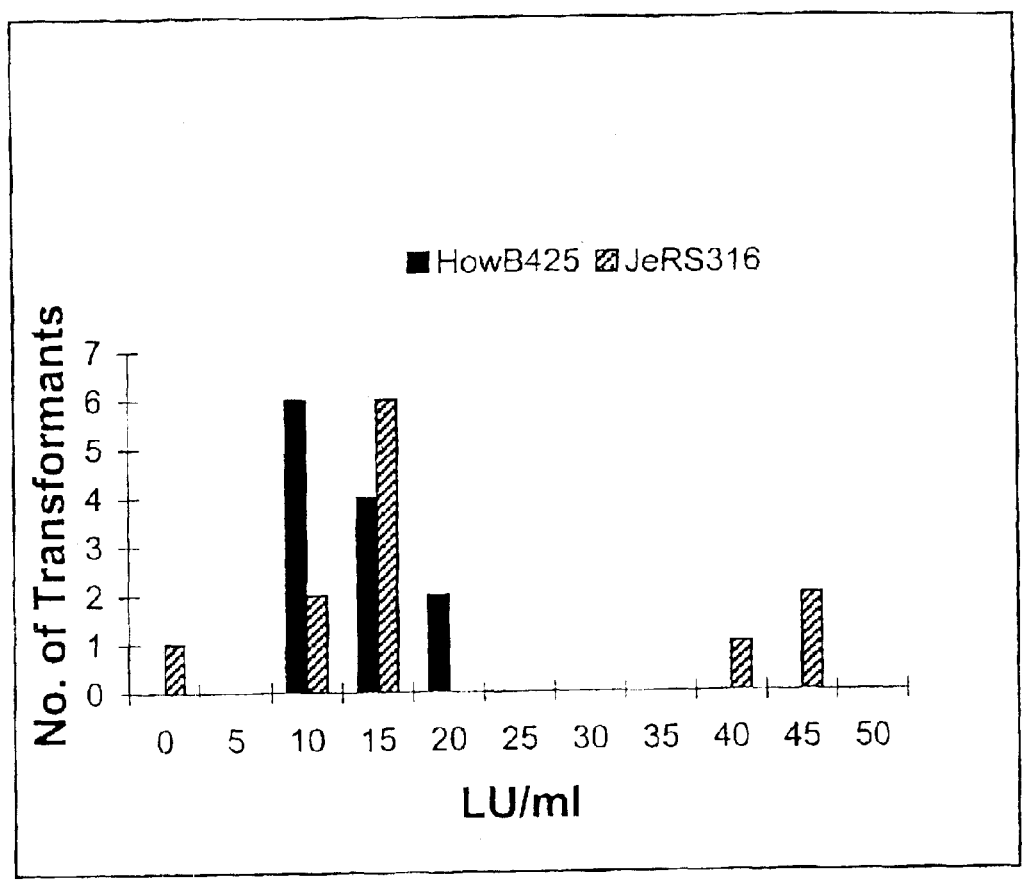
FIG. 3 shows a graphic illustration of the distribution of lipase expression in HowB425 (control) and JeRS316 (mutant) transformants.
Figure 4:
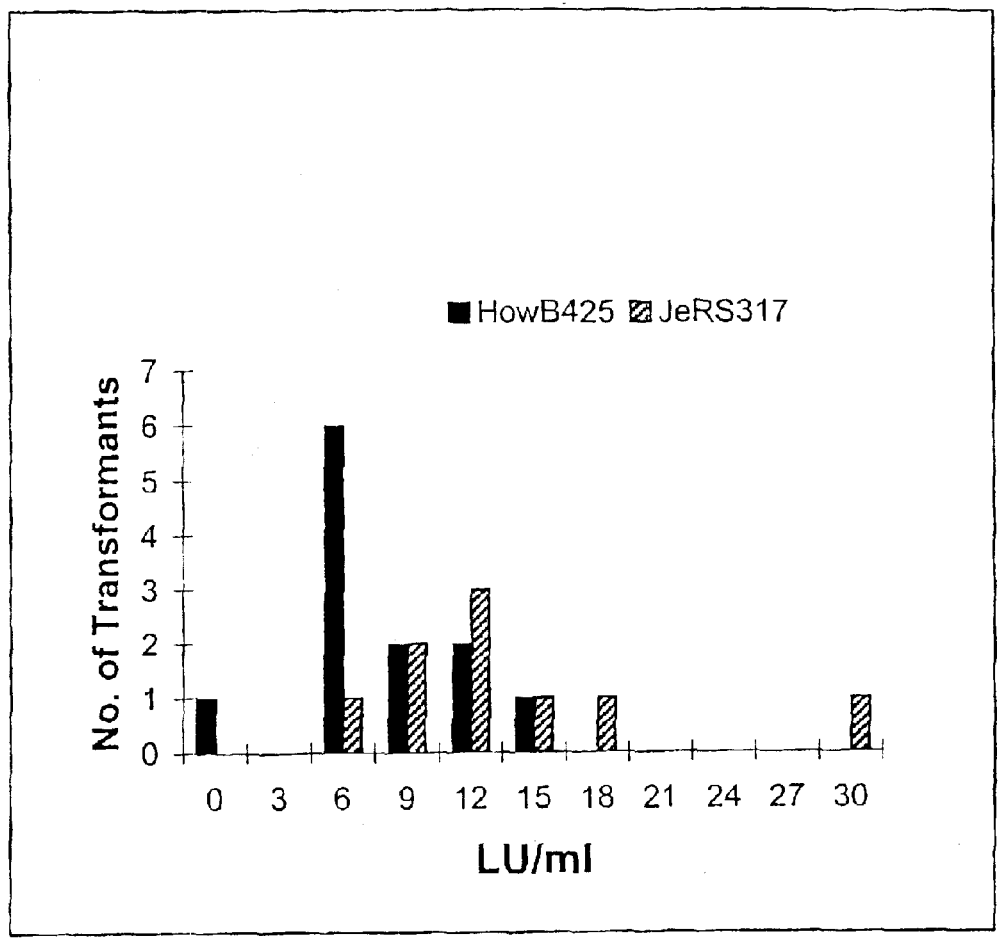
FIG. 4 shows a graphic illustration of the distribution of lipase expression in HowB425 (control) and JeRS317 (mutant) transformants.

The results are shown in Table II. A graphic representation of two of the mutants is shown in FIGS. 3 and 4. Although it is typical that individual transformants obtained following the introduction of DNA expression plasmids into any given *Aspergillus oryzae* host will vary in their ability to produce and secrete a heterologous polypeptide, and the number of transformants in each mutant strain is fairly small, the expression profiles for mutants JeRS316 (FIG. 3) and JeRS317 (FIG. 4) appear to be shifted further to higher lipase expression values as compared with the control.

TABLE II

Lipolase ® Expression in Morphological Mutants

| Strain | number of transformants | Mean (LU/ml) | Standard of Deviation (LU/ml) | Median (LU/ml) | Max (LU/ml) |
|---|---|---|---|---|---|
| Experiment A | | | | | |
| HowB425 | 12 | 6.49 | 3.28 | 5.47 | 12.10 |
| JeRS305 | 8 | 2.11 | 2.64 | 0.62 | 6.61 |
| JeRS306 | 12 | 7.44 | 5.49 | 6.57 | 15.40 |
| JeRS307 | 10 | 8.31 | 6.49 | 6.74 | 24.00 |
| JeRS313 | 5 | 4.54 | 3.84 | 2.40 | 8.98 |
| JeRS315 | 6 | 8.96 | 8.60 | 7.27 | 25.80 |
| JeRS317 | 9 | 12.20 | 6.85 | 10.97 | 28.00 |
| JeRS318 | 9 | 1.53 | 3.68 | 0.00 | 11.20 |
| JeRS320 | 9 | 9.47 | 7.97 | 5.11 | 22.56 |
| Experiment B | | | | | |
| HowB425 | 12 | 12.10 | 4.04 | 11.40 | 20.00 |
| JeRS303 | 12 | 7.51 | 9.55 | 4.34 | 31.70 |
| JeRS304 | 10 | 12.90 | 11.30 | 9.60 | 36.50 |
| JeRS314 | 12 | 11.40 | 5.89 | 12.20 | 21.60 |
| JeRS316 | 12 | 18.00 | 15.00 | 13.40 | 44.50 |

Example 6

Fermentation of *Aspergillus oryzae* Mutant JeRS316

To determine if the morphology mutants exhibit a superior fermentation behavior in comparison with the parent wild type morphology strain, one transformant each of the parent strain *Aspergillus oryzae* HowB425 and the mutant strain JeRS316 transformed with plasmid pJeRS23 are grown in a tank fermenter under fermentation conditions.

Figure 5:
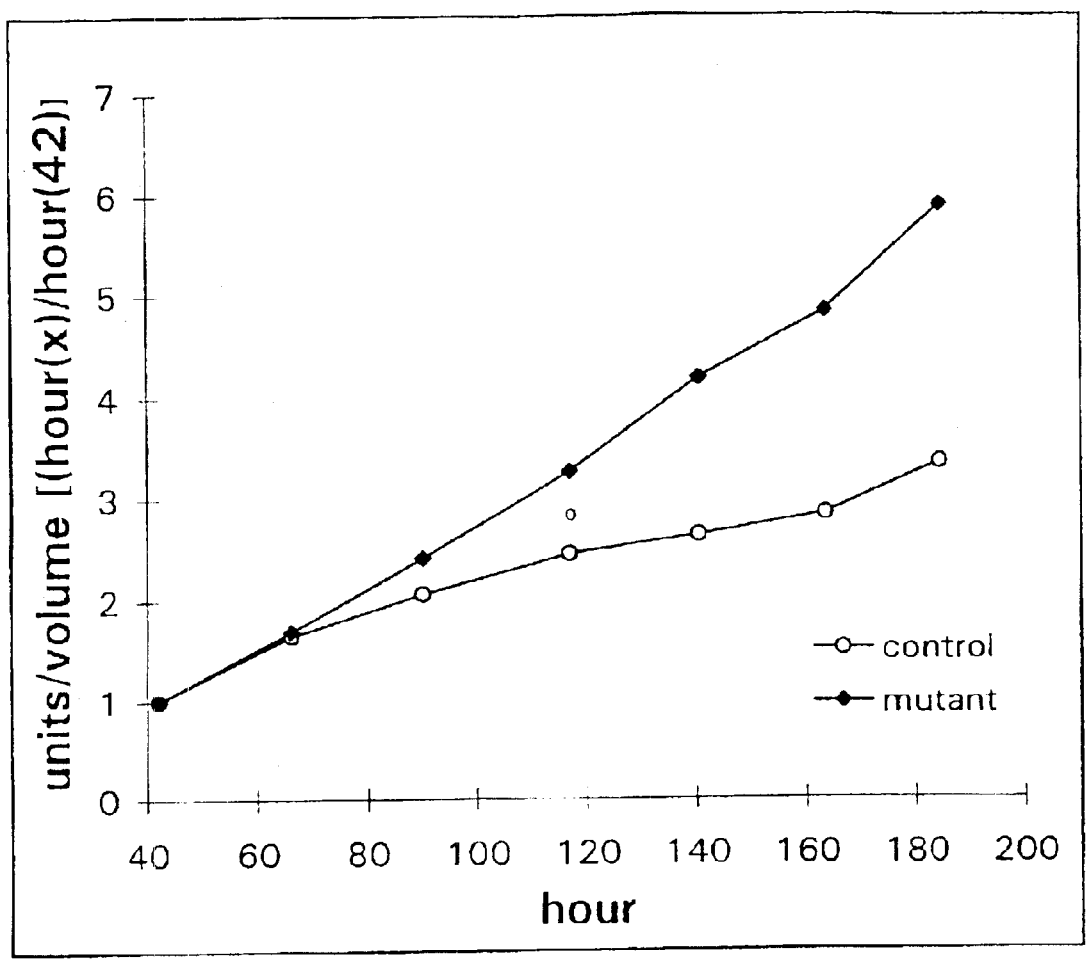
FIG. 5 shows a comparison of the heterologous lipase productive phase of the fermentation of control strain vs. mutant strain.

The morphology of the control culture at the end of the fermentation is typical for *Aspergillus oryzae* grown under these conditions. The culture is very viscous with a thick and grainy slow mixing appearance. Large air bubbles are visible in the tank. In contrast, the JeRS316 transformant displays a low viscosity, filamentous, easy mixing morphology with a small degree of pellet formation throughout the fermentation. Large air bubbles are not routinely observed in the tank. The expression of the heterologous lipase is examined and the results are shown in FIG. 5. If the mutant is superior to the parent in fermentation, the expectation is that the productive phase of the fermentation would be extended for the mutant. The results are reported as the ratio of [lipase titer in the culture broth at time (x)]/[lipase titer at time (42 hours)]. This analysis normalizes the expression data for the fact that not all transformants are equivalent in their absolute level of expression. As predicted for an improved morphology mutant, the heterologous polypeptide productive phase of the fermentation is extended significantly in strain JeRS316 as compared with the control. The final expression of the lipase in the broth of the morphology mutant culture is about five times higher in titer than the control.

Example 7

Construction of Fusarium expression vector pJRoy30

Figure 6:
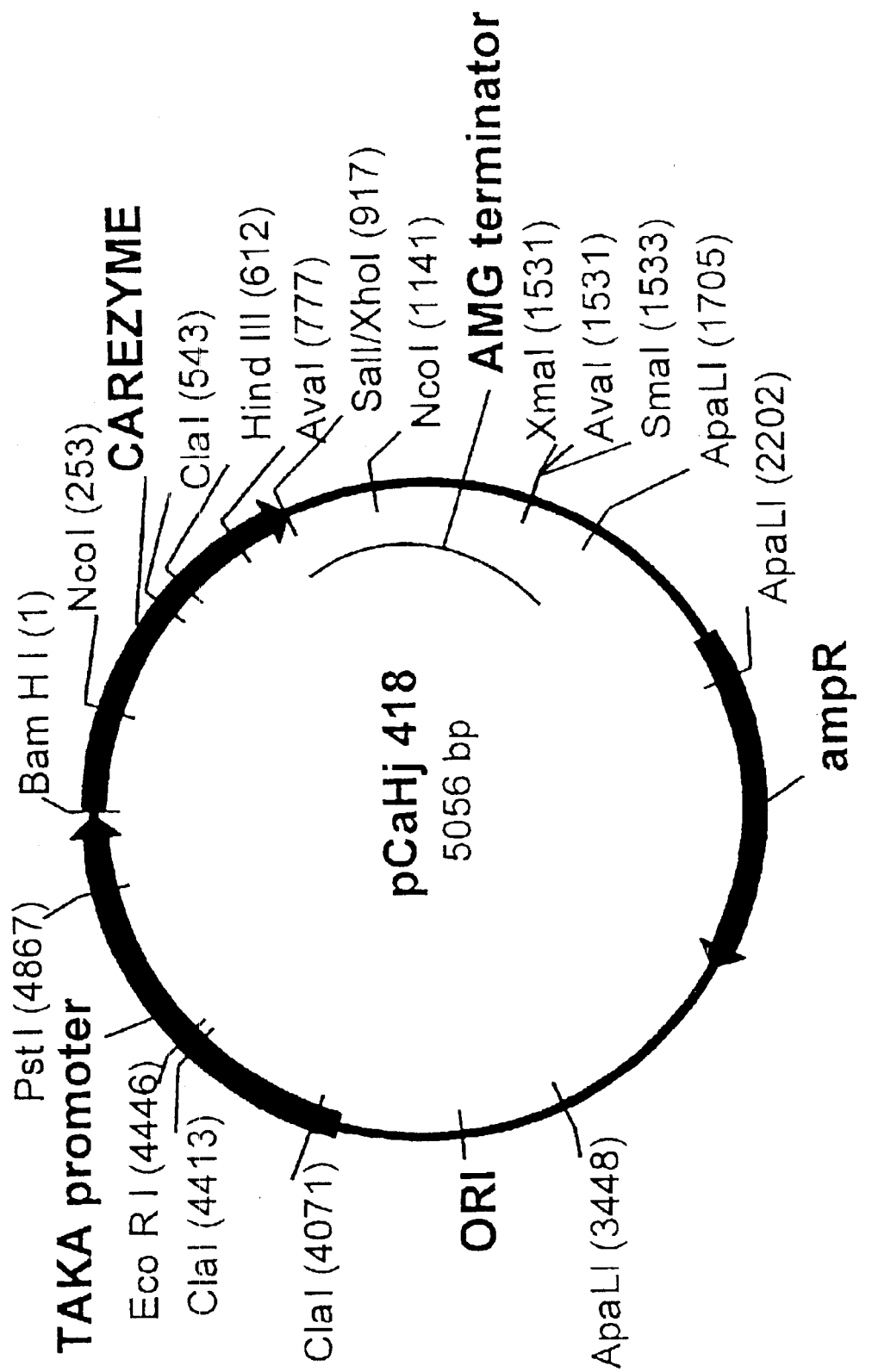
FIG. 6 shows a restriction map of pCaHj418.

The EcoRV site at −15 in the *Fusarium oxysporum* trypsin gene promoter of pJRoy20 (Royer et al., 1995, *Bio/Technology* 13: 1479–1483) and the NcoI site present at +243 in the CAREZYME™ (Novo Nordisk A/S, Bagsvaerd, Denmark) cellulase coding region are utilized to create an exact fusion between the *Fusarium oxysporum* trypsin gene promoter and the CAREZYME™ cellulase gene. A PCR fragment containing −18 to −1 of the *Fusarium oxysporum* trypsin gene promoter directly followed by −1 to +294 of the CAREZYME™ cellulase gene is generated from the CAREZYME™ vector pCaHj418 (see FIG. 6) using the following primers:

FORWARD
EcoRV                                          SEQ ID NO:1.
5' ctcttggatatctatctcttcaccATGCGTTCCTCCCCCCTCCT 3'

REVERSE
5' CAATAGAGGTGGCAGCAAAA 3'                     SEQ ID NO:1.

Lower case letters in the forward primer are bp −24 to −1 of the *Fusarium oxysporum* trypsin gene promoter, while upper case letters are bp 1 to 20 of CAREZYME™.

Figure 7:
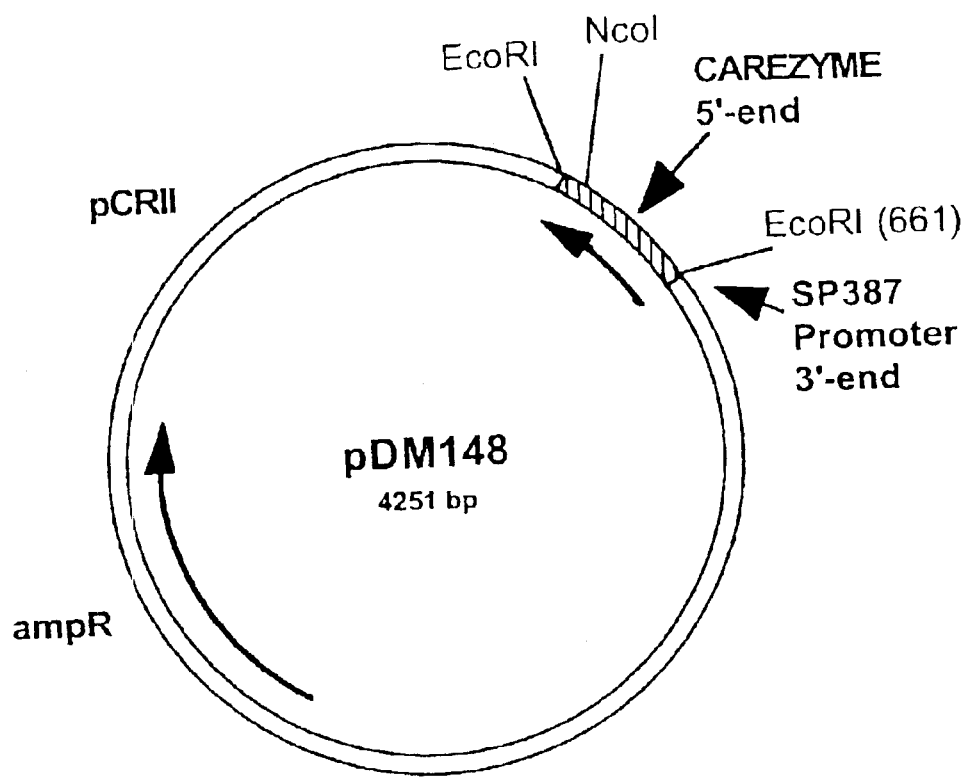
FIG. 7 shows a restriction map of pDM148.
Figure 8:
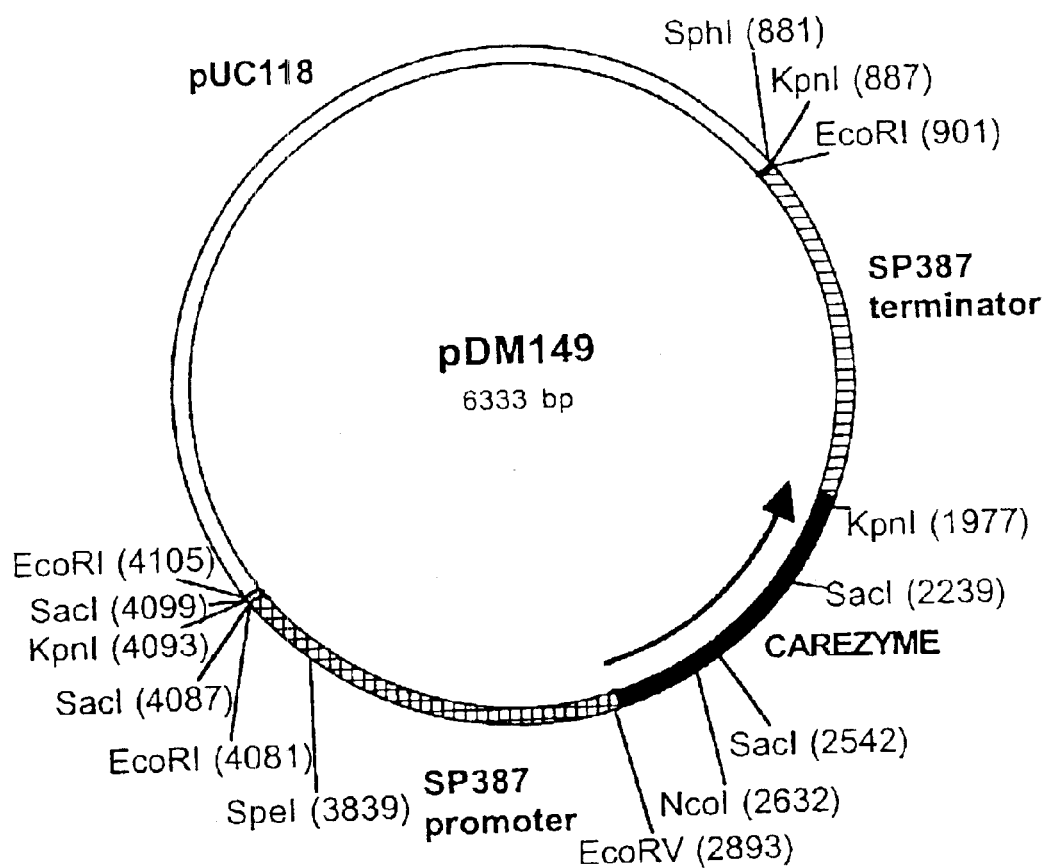
FIG. 8 shows a restriction map of pDM149.
Figure 9:
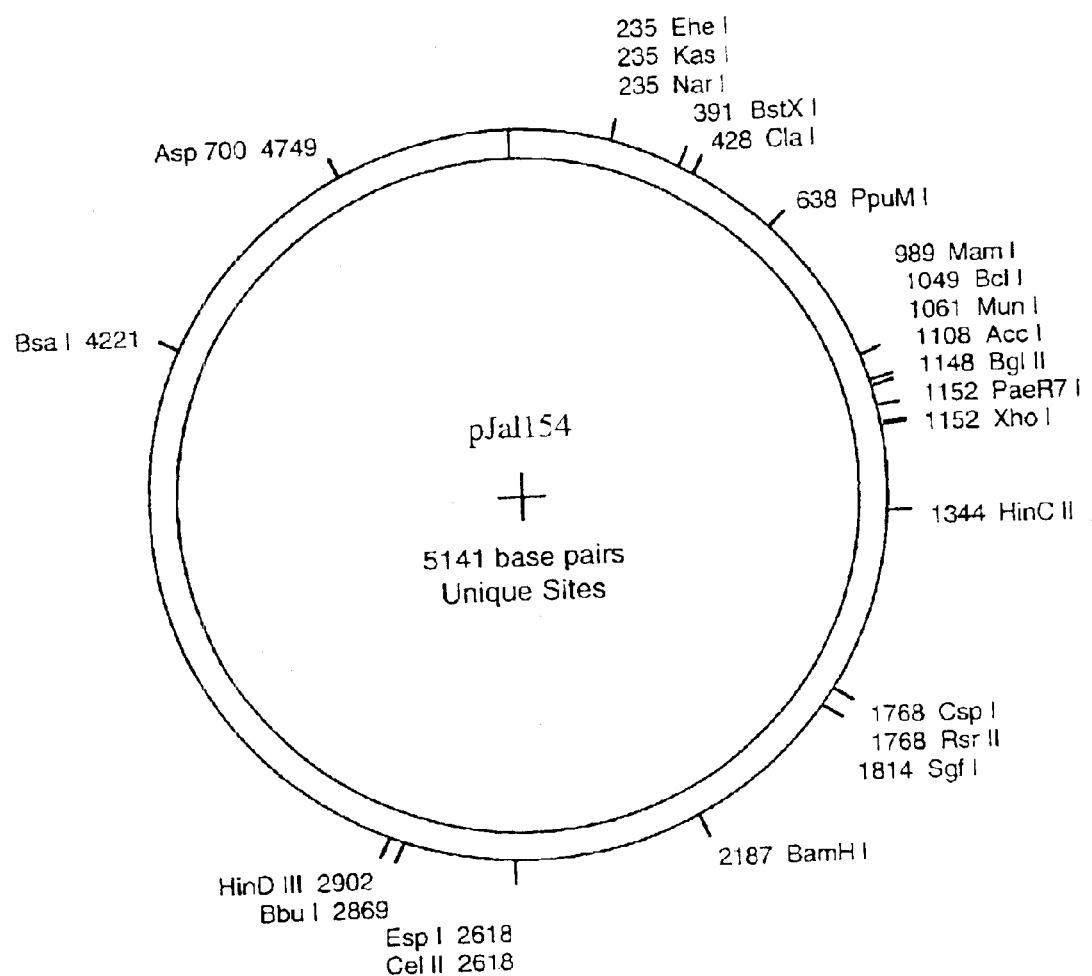
FIG. 9 shows a restriction map of pJaL154.
Figure 10:
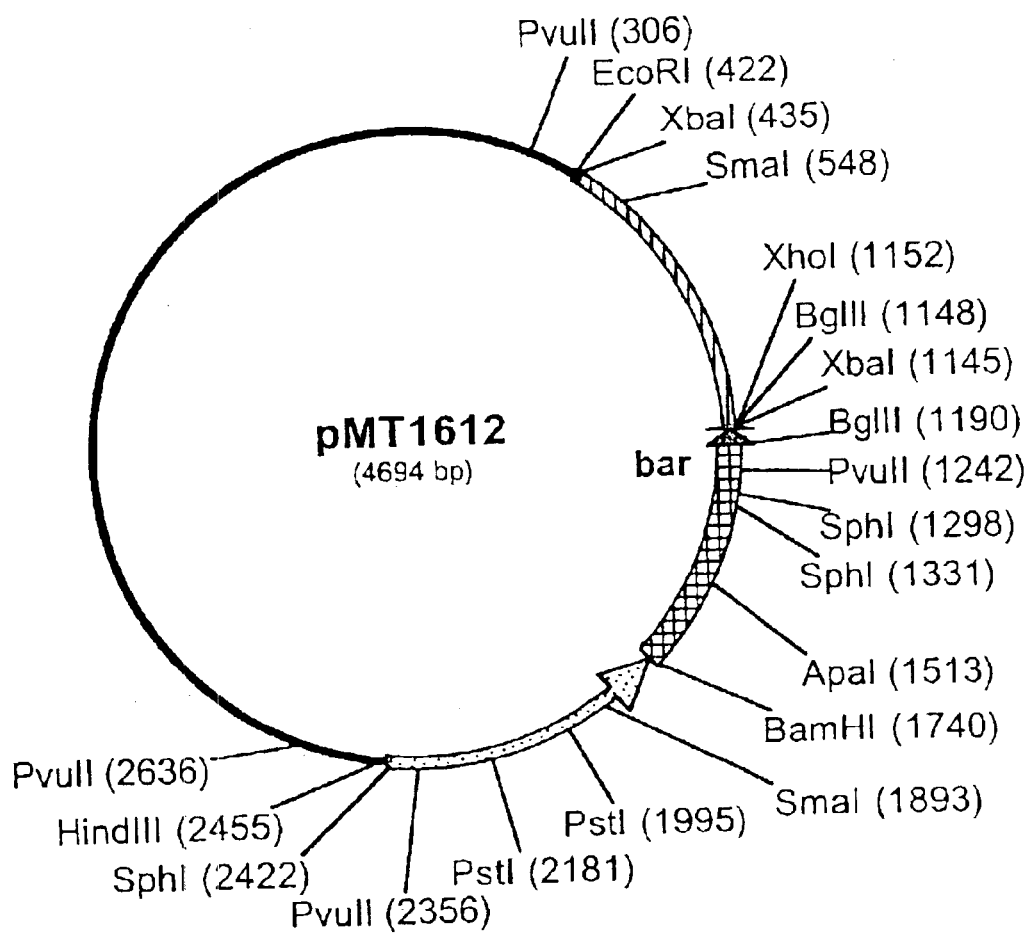
FIG. 10 shows a restriction map of pMT1612.
Figure 11:
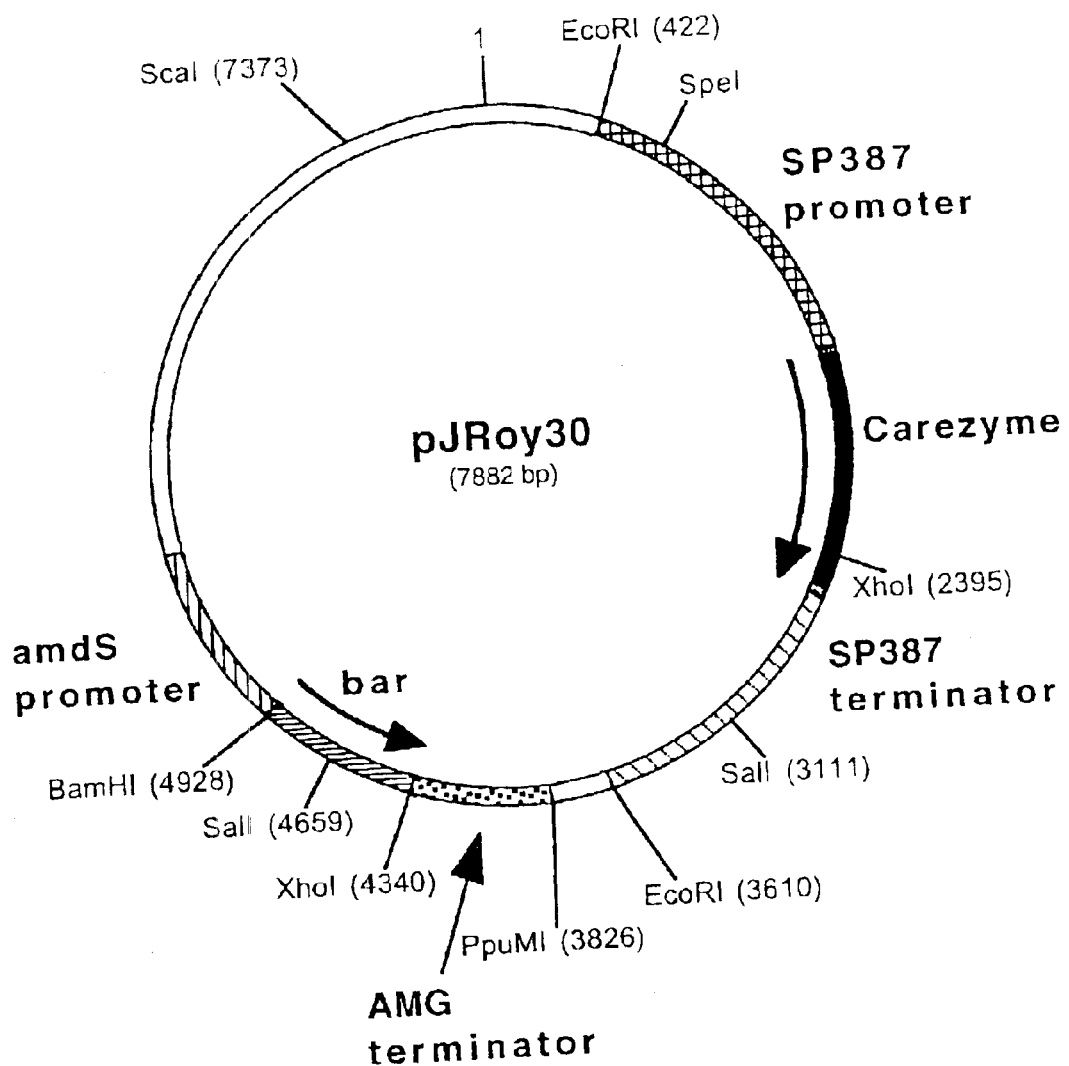
FIG. 11 shows a restriction map of pJRoy30.

The PCR conditions used are 95° C. for 5 minutes followed by 30 cycles each at 95° C. for 30 seconds, 50° C. for 1 minute, and 72° C. for 1 minute. The resulting 0.32 kb fragment is cloned into vector pCRII using Invitrogen's TA Cloning Kit (Invitrogen, La Jolla, Calif.) resulting in pDM148 (see FIG. 7). The 0.26 kb EcoRV/NcoI fragment is isolated from pDM148 and ligated to the 0.69 kb NcoI/BglII fragment from pCaHj418 and cloned into EcoRV/BamHI digested pJRoy20 to create pDM149 (see FIG. 8).

pMT1612 is constructed by introducing a 575 bp BamH1 BamH1 fragment containing the bar gene from pBIT (Straubinger et al., 1992, *Fungal Genetics Newsletter* 39:82–83) into pIC19H (Marsh et al., 1984, *Gene* 32:481–485) cut with BamHI/BglII. The bar gene is then isolated as a BamH1-XhoI fragment and inserted into BamHI-XhoI cut pJaL154 (FIG. 9) to generate pMT1612 (FIG. 10). The 3.2 kb EcoR1 CAREZYME™ cellulase expression cassette is transferred from pDM149 into EcoR1 cut basta marker pMT1612 to generate pJRoy30 (FIG. 11).

Example 8

Transformation of Fusarium

Fusarium strain A3/5 (ATCC 20334) and Fusarium strain A3/5 highly branched morphological mutants CC1-3, CC1-8, CC2-3, and MC3-5 (Wiebe et al., 1992, *Mycological Research* 96:555–562) are grown on 10×15 mm petri plates of Vogels medium (Vogel, 1964, *Am. Nature* 98:435–446) plus 1.5% glucose and agar for 3 weeks at 25° C. Conidia (approximately $10^8$ per plate) are dislodged in 10 ml of sterile water using a transfer loop and purified by filtration through 4 layers of cheesecloth and finally through one layer of Miracloth. Conidial suspensions are concentrated by centrifugation. Fifty ml of YPG medium comprised of 1% yeast extract, 2% bactopeptone, and 2% glucose are inoculated with $10^8$ conidia, and incubated for 14 hours at 24° C., 150 rpm. Resulting hyphae are trapped on a sterile 0.4 μm filter and washed successively with sterile distilled water and 1.0 M $MgSO_4$. The hyphae are resuspended in 10 ml of NOVOZYM 234™ solution (2–10 mg/ml in 1.0 M $MgSO_4$) and digested for 15–30 minutes at 34° C. with agitation at 80 rpm. Undigested hyphal material is removed from the resulting protoplast suspension by successive filtration through 4 layers of cheesecloth and through Miracloth. Twenty ml of 1 M sorbitol are passed through the cheesecloth and Miracloth and combined with the protoplast solution. After mixing, protoplasts (approximately $5 \times 10^8$) are pelleted by centrifugation and washed successively by resuspension and centrifugation in 20 ml of 1 M sorbitol and in 20 ml of STC. The washed protoplasts are resuspended in 4 parts STC and 1 part SPTC at a concentration of $1-2 \times 10^8$/ml. One hundred μl of protoplast suspension are added to 5 μg pJRoy30 and 5 μl heparin (5 mg/ml in STC) in polypropylene tubes (17×100 mm) and incubated on ice for 30 minutes. One ml of SPTC is mixed gently into the protoplast suspension and incubation is continued at room temperature for 20 minutes. Twenty five ml of molten solution (cooled to 40° C.) consisting of COVE salts, 25 mM $NaNO_3$, 0.8 M sucrose and 1% low melting agarose (Sigma Chemical Company, St. Louis, Mo.) are mixed with the protoplasts and then plated onto an empty 150 mm petri plate. Incubation is continued at room temperature for 10 to 14 days. After incubation at room temperature for 24 hours, 25 ml of the identical medium plus basta (5 mg/ml) are overlayed onto the petri plate. Basta is obtained from AgrEvo (Hoechst Schering, Rodovre, Denmark) and is extracted twice with phenol:chloroform:isoamyl alcohol (25:24:1), and once with chloroform:isoamyl alcohol (24:1) before use.

Example 9

Expression of Cellulase Activity

Transformants of Fusarium A3/5, CC1-3, CC2-3, and MC3-5 are cultured on M400Da medium in microtiter plates and shake flasks for 7 days at 37° C. One transformant each of Fusarium A3/5, CC1-3, CC2-3, and MC3-5 are cultivated in fermentors under suitable fermentation conditions in a medium containing typical carbon and nitrogen sources as well as mineral salts and trace metals.

Cellulase activity is measured using the following procedure. Volumes of 5 μl of various dilutions of a cellulase standard and 1–5 μl of samples are pipetted into a 96-well plate. The cellulase standard (CAREZYME™, Novo Nordisk A/S, Bagsvaerd, Denmark) is diluted to 150, 100, 50, 25, 12.5 and 6.25 ECU/ml in 100 mM MOPS pH 7.0. The substrate is prepared by dissolving azo-carboxymethylcellulose (Azo-CMC) at 2% w/v in 100 mM MOPS pH 7.0 and stirring at 80° C. for 10 minutes. A volume of 65 microliters of the azo-CMC substrate solution is pipetted into each of the sample wells and mixed. The 96-well plate is incubated in a water bath at 45° C. for 30 minutes and is then placed on ice for 2 minutes. A volume of 175 microliters of stop reagent is added to each well and mixed well. The stop reagent is prepared by suspending 0.2 g of $ZnCl_2$ in 20 ml of 0.25 M MOPS pH 7.0 and adding the suspension to 80 ml of acidified ethanol containing 1.1 ml of concentrated HCl per liter of ethanol. The 96-well plate is centrifuged at 3000 rpm for 10 minutes in a Sorval RT 6000B centrifuge. After centrifugation is complete, 50 μl of each supernatant is transferred to a new 96-well plate containing 50 μl of water per well. The absorbance at 600 nm is measured.

The results for the microtiter plate, shake flask, and fermentor cultures are presented in Table III where the maximum cellulase yield is normalized to 1.0. In microtiter plate culture, transformants of CC2-3 and MC3-5 produce levels of cellulase which are 22% and 46% higher, respectively, compared to the parent strain. In shake flask culture, transformants of CC1-3, CC2-3 5, and MC3-5 produce levels of cellulase which are 85%, 54%, and 7% higher, respectively, compared to the parent strain. In fermentors, of CC1-3, CC2-3 5, and MC3-5 produce levels of cellulase which are 136%, 3%, and 8% higher, respectively, compared to the parent strain.

TABLE III

Production of cellulase by transformants of the wild type strain (A3/5) and morphological mutants (CC1-3, CC2-3, and MC3-5).

| Host | Microtiter Plate | | Shake Flask | | Fermentor | |
| --- | --- | --- | --- | --- | --- | --- |
| | Maximum° | n* | Maximum | n | Maximum | n |
| A3/5 | 1.0 | 5 | 1.0 | 6 | 1.0 | 1 |
| CC1-3 | 0.29 | 4 | 1.85 | 2 | 2.36 | 1 |
| CC2-3 | 1.22 | 1 | 1.54 | 1 | 1.03 | 1 |
| MC3-5 | 1.46 | 2 | 1.07 | 2 | 1.08 | 1 |

°The maximum cellulase yield of the Fusarium A3/5 parent strain is normalized to 1.0 for the highest activity observed under each set of growth conditions. *n represents the number of transformants analyzed.

---

What is claimed is:

1. A method for obtaining a mutant cell which produces a heterologous protein, comprising:
   (a) producing a first population of presumptive mutant cells from an Neurospora parent cell;
   (b) identifying from the first population a second population of presumptive mutant cells having a more restricted colonial phenotype or a more extensive hyphal branching than the parent cell; and
   (c) identifying from the second population the mutant cell, comprising a nucleic acid sequence encoding a heterologous polypeptide, which has a radial extension rate which is at least 10% less than the parent cell, has a hyphal growth unit length that is at least 10% less than the parent cell, and has one or more improved properties selected from the group consisting of (i) produces at least about 10% more heterologous polypeptide than the parent cell, (ii) exhibits about 90% or less of the viscosity of the parent cell, and (iii) secretes more heterologous protein than the parent cell, when cultivated under the same conditions; and
   (d) obtaining the mutant cell.

2. The method of claim 1, wherein in step (b), the second population of presumptive mutant cells has a more restricted colonial phenotype and a more extensive hyphal branching than the parent cell.

3. The method of claim 1, wherein the radial extension rate is at least 20% less than the parent cell.

4. The method of claim 1, wherein the hyphal growth unit length is at least 20% less than the parent cell.

5. The method of claim 1, wherein the mutant cell produces at least about 10% more heterologous polypeptide than the parent cell.

6. The method of claim 1, wherein the mutant cell exhibits about 90% or less of the viscosity of the parent cell.

7. The method of claim 1, wherein the mutant cell has a further improved property of an improved growth.

8. A method for producing a heterologous polypeptide, comprising:
   (a) cultivating a mutant cell of an Neurospora parent cell under conditions suitable for production of the heterologous polypeptide, wherein the mutant cell comprises a nucleic acid sequence encoding the heterologous polypeptide, and wherein the mutant cell has a radial extension rate which is at least 10% less than the parent cell, has a hyphal growth unit length that is at least 10% less than the parent cell, and has one or more improved properties selected from the group consisting or (i) produces at least about 10% more heterologous polypeptide than the parent cell, (ii) exhibits about 90% or less of the viscosity of the parent cell, and (iii) secretes more heterologous protein than the parent cell, when cultivated under the same conditions; and
   (b) recovering the heterologous polypeptide.

9. The method of claim 8, wherein the radial extension rate is at least 20% less than the parent cell.

10. The method of claim 8, wherein the hyphal growth unit length is at least 20% less than the parent cell.

11. The method of claim 8, wherein the mutant cell produces at least about 10% more heterologous polypeptide than the parent cell.

12. The method of claim 8, wherein the mutant cell exhibits about 90% or less of the viscosity of the parent cell.

13. The method of claim 8, wherein the mutant cell has a further improved property of an improved growth.

14. A mutant cell of an Neurospora parent cell comprising a nucleic acid sequence encoding a heterologous polypeptide, wherein the mutant cell has a radial extension rate which is at least 10% less than the parent cell, has a hyphal growth unit length that is at least 10% less than the parent cell, and has one or more improved properties selected from the group consisting of (i) produces at least about 10% more heterologous polypeptide than the parent cell, (ii) exhibits about 90% or less of the viscosity of the parent cell, and (iii) secretes more heterologous protein than the parent cell, when cultivated under the same conditions.

15. The mutant cell of claim 14, wherein the radial extension rate is at least 20% less than the parent cell.

16. The mutant cell of claim 14, wherein the hyphal growth unit length is at least 20% less than the parent cell.

17. The mutant cell of claim 14, wherein the mutant cell produces at least about 10% more heterologous polypeptide than the parent cell.

18. The mutant cell of claim 14, wherein the mutant cell exhibits about 90% or less of the viscosity of the parent cell.

19. The method of claim 14, wherein the mutant cell has a further improved property of an improved growth.

* * * * *

SEQUENCE LISTING

<160> NUMBER OF SEQ ID NOS: 2

<210> SEQ ID NO 1
<211> LENGTH: 44
<212> TYPE: DNA
<213> ORGANISM: Fusarium oxysporum

<400> SEQUENCE: 1
ctcttggata tctatctctt caccatgcgt tcctccccc tcct    44

-continued

```
<210> SEQ ID NO 2
<211> LENGTH: 20
<212> TYPE: DNA
<213> ORGANISM: Fusarium oxysporum

<400> SEQUENCE: 2
caatagaggt ggcagcaaaa                                                   20
```